(12) United States Patent
Milbocker

(10) Patent No.: US 8,604,099 B2
(45) Date of Patent: *Dec. 10, 2013

(54) IN SITU BULKING COMPOSITION

(75) Inventor: Michael T. Milbocker, Holliston, MA (US)

(73) Assignee: Promethean Surgical Devices, East Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/422,448

(22) Filed: Mar. 16, 2012

(65) Prior Publication Data

US 2013/0035415 A1  Feb. 7, 2013

Related U.S. Application Data

(60) Division of application No. 13/017,129, filed on Jan. 31, 2011, now abandoned, which is a division of application No. 11/411,283, filed on Apr. 26, 2006, now Pat. No. 7,927,619, which is a continuation-in-part of application No. 09/939,863, filed on Aug. 27, 2001, now Pat. No. 7,044,982, which is a continuation-in-part of application No. 09/692,963, filed on Oct. 20, 2000, now Pat. No. 6,296,607.

(51) Int. Cl.
*A61L 24/04* (2006.01)
*C08L 75/04* (2006.01)

(52) U.S. Cl.
USPC .................................................. 523/113

(58) Field of Classification Search
None
See application file for complete search history.

(56) References Cited

U.S. PATENT DOCUMENTS

| | | | | | |
|---|---|---|---|---|---|
| 4,049,592 | A | * | 9/1977 | Marans et al. | 521/159 |
| 5,064,653 | A | * | 11/1991 | Sessions et al. | 424/445 |
| 5,091,176 | A | * | 2/1992 | Braatz et al. | 424/78.17 |
| 5,328,955 | A | * | 7/1994 | Rhee et al. | 525/54.1 |
| 5,792,478 | A | * | 8/1998 | Lawin et al. | 424/502 |
| 6,818,018 | B1 | * | 11/2004 | Sawhney | 623/11.11 |
| 7,128,927 | B1 | * | 10/2006 | Dunn | 424/423 |

* cited by examiner

*Primary Examiner* — Robert A Wax
*Assistant Examiner* — Danah Al-Awadi
(74) *Attorney, Agent, or Firm* — Novak Druce Connolly Bove + Quigg LLP

(57) ABSTRACT

The present invention relates to a hydrated, biocompatible tissue-augmentation compound and methodology for its implantation into mammalian tissue. The tissue-augmentation compound is comprised of: living tissue, optionally body derived fluids, and at least one NCO-terminated hydrophilic urethane prepolymer derived from an organic polyisocyanate, and oxyethylene-containing diols or polyols in which essentially all of hydroxyl groups are capped with polyisocyanate.

11 Claims, No Drawings

IN SITU BULKING COMPOSITION

PRIORITY

This application is a divisional of and claims priority to 13/017,129, filed Jan. 31, 2011 now abandoned which is a divisional of and claims priority to U.S. Ser. No. 11/411,283, filed Apr. 26, 2006, now U.S. Pat. No. 7,927,619, which is a continuation-in-part of application Ser. No. 09/939,863, filed Aug. 27, 2001, now U.S. Pat. No. 7,044,982, which is a continuation-in-part of application Ser. No. 09/692,963, filed Oct. 20, 2000, now U.S. Pat. No. 6,296,607, all commonly owned and having common inventorship. Each of these applications and patents is incorporated herein in its entirety by reference.

BACKGROUND OF THE INVENTION

1. Field of the Invention

The invention relates to methods and substances comprising a biocompatible, non-degradable polymer of stable volume for the purpose of augmenting mammalian tissue.

2. Background

This invention relates to synthetic surgical tissue adhesives, tissue sealants and tissue bulking agents, created by reacting an adhesive tissue reactive injectable with living in situ tissue. More specifically, a tissue cross-linked polyurea-urethane bond is formed by reaction of isocyanate capped alkylene oxide diols, triols or polyols with living tissue forms an immobilized, non-biodegradable augmentation of tissue.

Numerous bulking and plastic surgery applications and patents have been published, but none of them teach bulking by means of the novel substance disclosed here and further none of them provide adhesion to tissue. Thus, in the prior art, there is susceptibility to implant migration because of lack of adhesion. Moreover, the present invention is biocompatible. Prior art bulking substances are also known to be biocompatible, but they are also biodegradable. Biodegradability of an implant in a tissue augmentation procedure is generally not desirable since the benefits conferred by the implanted substance disappear with time.

U.S. Pat. No. 5,785,642 (Wallace et al.) describes a 3-part injectable polymer for treating incontinence. While the patent claims improved resistance to migration, principally when compared with particulate injectables, it does not describe a tissue bond to guard against implant migration. Furthermore, the disclosed invention involves forming a polymer precipitate in situ from a solvent/polymer system. Since the solvent does not entirely become part of the precipitate, then some of the injected solvent volume is eventually lost to absorption into the surrounding tissue. Thus, the invention does not teach a device which has a stable volume once implanted.

U.S. Pat. No. 5,712,252 (Smith) describes a method of augmenting soft tissue in a mammal, which includes injecting keratin into soft tissue. Keratin is a biodegradable substance.

U.S. Pat. No. 5,763,399 (Lee) describes a composition and method for effective revitalization of scar tissue by injecting a bioactive substance having angiogenic activity. The revitalization of scar tissue is intended to augment existing tissue. However, this invention cannot control the extent of augmentation.

U.S. Pat. No. 5,922,025 (Hubbard) describes a permanent, biocompatible material for soft tissue augmentation. The biocompatible material comprises a matrix of smooth, round, finely divided, substantially spherical particles of a biocompatible ceramic material. However, prevention of migration of the ceramic material is not described.

U.S. Pat. No. 5,976,526 (Atala) describes treatment of vesicoureteral reflux, incontinence and other defects using an injectable of bladder cells mixed with a liquid polymeric material. This material is susceptible to biodegradation.

U.S. Pat. No. 5,855,615 (Bley at al) describes a composition for injecting into the urethra comprising a plurality of physiologically acceptable solid polymer particles dispersed in a physiologically acceptable biodissipatable liquid carrier. The solid polymer particles are capable of hydrating to a predetermined volume. The injection volume is therefore not necessarily the same as the final hydrated volume.

U.S. Pat. No. 5,709,854 (Griffith-Cima et al) describes a cell polymeric solution that self-cross-links, but does not bond to tissue, for the purpose of inducing tissue formation.

One of the primary uses of the present invention is treatment of urinary incontinence. In particular, many women suffer from incontinence caused by childbirth or obesity. The initial treatment for stress incontinence is exercise to strengthen the pelvic floor muscles. If these exercises are ineffective, open surgical repair of the bladder neck is often attempted. Such surgical repair procedures are not successful for all patients. There is also risk associated with open surgical procedures, such as trauma, infection, and risks of anesthesia.

As an alternative to surgical repair, urinary incontinence has been treated by injecting various substances into the tissue surrounding the urethra, i.e., the periurethral tissue, to add bulk to this tissue. The aim of this treatment is to compress the urethra at the level of the bladder neck to impede involuntary flow of urine from the bladder.

Murless has reported the use of sodium morrhuate for the treatment of stress incontinence (J. Obstet. Gynaecol., 45:67-71 (1938)). This material was not successful in treating incontinence and pulmonary infarction was an observed complication. Paraffin (Acta Urol. Belg., 23:259-262 (1955)) and other sclerosing solutions (Urol. Int., 15:225-244 (1963)) have been tried yielding poor results.

Polytetrafluoroethylene particles (TEFLON™, POLYTEF™) have been used as injectable bulking material with a success rate from 30% to 86% in some studies (J. Urol., 111:180-183 (1974); Br. J. Urol., 55:208-210 (1983) 210 (1983); BMJ 228; 192 (1984); J. Urol., (Paris), 62:39-41 (1987); Br. J. Urol., 62:39-41 (1988); Aust. N. Z. J. Surg., 61:663-666 (1966)). The complications associated with this procedure were foreign body granulomas that tended to migrate to distant organs, such as the lungs, liver, spleen and brain (JAMA, 251:3227-3281 (1984)).

Another injectable used recently is glutaraldehyde cross-linked bovine dermal collagen (Med. J. Aust., 158:89-91 (1993); Br. J. Urol., 75:359-363 (1995); Br. J. Urol., 75: 538-542 (1993)). A major problem with the use of collagen was biodegradation with associated decrease in implant volume over time necessitating retreatment (J. Urol., 150:745-747 (1993)). Collagen can also cause adverse immune responses and allergic reactions to bovine collagen have been described (Br. J. Urol., 75:359-363 (1995)).

Other materials have been suggested for use in the treatment of vesicourectal reflux. These substances include polyvinyl alcohol foam (J. Urol., 144:531-533 (1990)), glass particles (J. Urol., 148:645 (1992)), a chondrocyte-alginate suspension (J. Urol., 150:745-747 (1993)) and a detachable silicone balloon (J. Urol., 148:724-728 (1992)), each of these cited journal article being incorporated herein by reference.

Injectables have not been suggested for treatment of gastroesophageal reflux disease (GERD), but such use of the disclosed material of this application is envisioned. The material may be injected into the wall of the esophagus to thicken the wall and narrow the gastroesophageal junction into the stomach.

In addition to the need for an immobilized, volume-constant, biocompatible implant, there is also a need to be able to visualize the volume of injected material during and after implantation. It would be preferred to monitor the implant size by non-invasive means. Furthermore, fluoroscopic imaging of the implant would aid in estimation of the implant size and location if follow-up injections are necessary.

In addition, polymerization time of the injected material is an important parameter since the material is typically delivered as a low viscosity solution that may leak from the site after needle removal. The lower the viscosity of the injectable the smaller the needle that may be used.

Finally, there are several pragmatic considerations. For example, the injectable material should not polymerize in the needle of the delivery device so as to necessitate replacement of the needle during the procedure. The solution should be of low viscosity to enable easy delivery of the solution through a 23 G needle.

SUMMARY OF THE INVENTION

This invention is directed toward a composition that can be used for tissue bulking, tissue sealing and tissue adhesion or repair. These and related applications are collectively referred to as "tissue-augmenting" applications sand materials herein, unless specified otherwise.

The materials and techniques of the invention may also be used in applications where bulking of tissue provides a functional or an aesthetic result. Accordingly, in one of its aspects, this invention is directed to a method for treating urinary incontinence in a mammal, which method comprises delivery of a composition comprising a biocompatible prepolymer and a contrast agent to the periurethral tissue of a mammal. Similarly, the composition and methods can be used to treat gastroesophageal reflux. The may also be used to seal tissue to prevent leakage of blood or other bodily fluids. They may also be used to adhere tissue to tissue or to implants and the like.

It is an object of the present invention to provide a bulking, sealing or adhesive material that chemically bonds in situ to living tissue that is biocompatible, elastomeric, and non-biodegradable.

It is another object of this invention to provide a bulking, sealing or adhesive formulation for tissue augmentation and tissue surgery having short bonding and polymerization time.

It is another object of this invention to provide a bulking, sealing or adhesive material which is non-toxic and non-immunogenic.

It is another object of this invention to provide a low viscosity bulking, sealing or adhesive material permitting delivery through a 23 G needle.

It is another object of this invention to provide a bulking, sealing or adhesive material that does not undergo appreciable volume change acutely during polymerization or chronically after implantation in tissue.

It is another object of this invention that a bulking, sealing or adhesive material provide fluoroscopic contrast for noninvasive visualization during and after implantation.

It is another object of this invention to provide a prepolymer composition for bulking, sealing or adhesion that is gamma sterilizable without appreciable cross-linking of the prepolymer or altering its ability to form a hydrated tissue bond.

The tissue augmentation of this invention is achieved by reacting the target tissue with a solution of an ethylene oxide-based polyol, triol or diol end-capped with an organic polyisocyanate. The tissue augmenting agent of this invention may in particular be a polyisocyanate capped copolymer of ethylene oxide and propylene oxide, which may be a polyol, triol or diol.

The tissue augmenting agent of this invention may additionally contain, at least during the process of application to tissue, viscosity lowering inert components such as Perfluronbon or physiologic saline.

It is one primary object of this invention to provide a tissue augmentation solution that is easily applied, cures quickly in situ, and produces a strong tissue bond. The preparations disclosed here can be stored at normal hospital room temperatures, and possess long shelf life.

The invention comprises a hydrated, biocompatible tissue-augmentation compound comprised of living tissue and at least one NCO-terminated hydrophilic urethane prepolymer. The compound may also incorporate body fluids, or other fluids including physiological saline, water and the like. The urethane prepolymer is derived from an organic polyisocyanate and oxyethylene-based diols or polyols, in which essentially all hydroxyl groups are capped with polyisocyanate, especially with low molecular weight diisocyanate. The prepolymer units are preferably oxyethylene-based diols or polyols capped with aliphatic or aromatic isocyanates. The molecular weight of the diols or polyols prior to capping with polyisocyanate is at least about 1000 D (daltons), and preferably at least about 3,000 D or more.

The polyisocyanate (diisocyanate or higher polyisocyanate) used for capping may be any physiologically-acceptable diisocyanate or higher polyisocyanate of commerce. For example, it may be a toluene diisocyanate. The polyisocyanate may be isophorone diisocyanate. The polyisocyanate may be a mixture of toluene diisocyanate and 6-chloro 2,4,5-trifluoro1,3 phenylene diisocyanate. The polyisocyanate may be a mixture of toluene diisocyanate and tetrafluoro1,3-phenylene diisocyanate. The polyisocyanate may be a mixture of diphenylmethane diisocyanate and 6-chloro 2,4,5-trifluoro1, 3 phenylene diisocyanate. The polyisocyanate may be a mixture of diphenylmethane diisocyanate and tetrafluoro-1,3-phenylene diisocyanate. The polyisocyanate may be paraphenylene diisocyanate.

The diols or polyols are preferably capped with polyisocyanate so that isocyanate is in excess. in one embodiment, the isocyanate-to-hydroxyl group ratio is between 1.5 and 2.5. The isocyanate concentration in the prepolymer units may be between 0.05 and 0.8 milliequivalents per gram.

The hydrated, biocompatible tissue-augmentation compound may further comprise a biocompatible solvent, not reactive with the isocyanate-capped polymer to control viscosity and cure time. Such agents are preferably added to the tissue-augmentation compound at the time of application. For example, the solvent may be comprised of acetone. The hydrated, biocompatible tissue-augmentation compound may further comprise a contrast agent comprised of meglumine. The hydrated, biocompatible tissue-augmentation may further comprise a low molecular weight uncapped polyethylene glycol, consisting of PEG 300 as a solvent. The hydrated, biocompatible tissue-augmentation compound may further comprise a contrast agent and a biocompatible solvent in combination.

The hydrated, biocompatible tissue-augmentation compound may further comprise physiological saline. The hydrated, biocompatible tissue-reactive compound may comprise between 10% and 30% of physiologic saline or other biocompatible fluid for many applications. The hydrated, biocompatible tissue reactive compound may comprise 10-20% physiologic saline or other biocompatible fluid for applications requiring high strength in the gel that is formed. The hydrated, biocompatible tissue-reactive compound may comprise up to at lest about 75% of physiologic saline or other biocompatible fluid when strength is less important, for example for sealing or coating tissue. The hydrated, biocompatible tissue-augmentation compound of may include an injectable material selected from the group comprised of collagen, silicone, teflon, or pyrolytic carbon coated beads.

The invention also includes a method of preparing a crosslinked hydrophilic, biocompatible hydrated tissue-augmentation compound by reacting together mammalian body tissue, body derived fluids and a prepolymer in a prepolymer-to-water ratio ranging from about 1:3 to about 20:1. The prepolymer is prepared by the steps of selecting diols or polyols from oxyethylene-based diols or polyols. The phrase "oxyethylene-based" as used herein includes polymers predominantly made from ethylene oxide monomers but optionally containing a minority percentage of higher alkylene oxides such as propylene oxide. The polyols have an average molecular weight of at least 1000, preferably 3,000 to about 30,000.

The selected diols or polyols are reacted with an aliphatic or aromatic polyisocyanate at an isocyanate-to-hydroxyl ratio of greater than 1.0, for example about 1.5 to 2.5, so that all of the hydroyl groups of said diols or polyols are capped with polyisocyanate and the resulting prepolymer has an isocyanate concentration of no more than about 0.8 milliequivalents per gram. The diols and polyols may be dissolved in an organic solvent, preferably selected from the group comprising acetonitrile and acetone. The hydrated tissue-augmentation compound may include a solution of non-body derived water, including a saline solution containing 0.9% NaCl. The prepolymer-to-water ratio may be between 1:3 to 20:1, i.e., a mixture of prepolymer with saline or water may contain from about 5% prepolymer by weight up to about 95% prepolymer by weight. The method may include the step of washing the bond with a polyfunctional diamine to end isocyanate reactivity.

The invention also includes a prepolymer solution for preparing a hydrophilic, biocompatible tissue augmentation compound characterized by volume conservation, and resistance to decomposition within the body, said prepolymer consisting of: oxyethylene-based dials or polyols having an average molecular weight in excess of 3,000, the diols or polyols having all of the hydroxyl groups capped with an aromatic or aliphatic diisocyanate; and an adhesive tissue augmentation injectable having polymeric polyisocyanates having an isocyanate concentration up to 0.8 meq/gm, and an additional liquid such as acetone, uncapped PEG, DMSO, or acetone, and optionally a contrast agent such as meglumine. The prepolymer may include a fluorine containing diisocyanate. The prepolymer may include a polyfunctional amine such as lysine to end isocyanate reactivity, applied after tissue contact. Application of the prepolymer may include the step of heating the compound to a temperature to between about 65-80 degrees C., and adding the heated compound to mammalian body tissue.

The invention also includes a method for treating urinary incontinence in a mammal comprising the steps of delivering a composition comprising a biocompatible prepolymer, a biocompatible solvent, and a contrast agent to the periurethral tissue of the mammal, wherein said prepolymer reacts with all available water at the site of injection and further wherein the delivery results in a polymer matrix of fixed volume formed in situ in the periurethral tissue thereby reducing urinary incontinence in the mammal. The method may further include the step of delivering the composition into the periurethral tissue by an endoscopic process, for example via an endoscope.

The invention also include a method for the delivery of a composition, wherein the composition includes a biocompatible prepolymer, a biocompatible solvent, and a water soluble contrast agent, to the periurethral tissue of a mammal, wherein said tissue already has deposited therein an initial amount of the composition. Said method further comprises visualizing the position of the deposited composition in the periurethral tissue; delivering a prepolymer composition to the periurethral tissue of a mammal containing said deposited composition; reacting the biocompatible polymer with all available water at the delivery site; and delivering additional prepolymer that bonds to the deposited mass incrementally to controllably increase the resistance of the flow of urine from the bladder. The method may include the step of visualizing the deposition of compound by selection of one of the processes of the group consisting of direct visualization, feel, fluoroscopy or ultrasound.

The invention also includes the method for further treating urinary incontinence in a mammal, comprising the steps of implanting a first biocompatible polymer matrix to a periurethral tissue site of a mammal; and then implanting a second biocompatible polymer matrix to said site at least one day after said first implanted biocompatible polymer matrix has been implanted at said site, wherein said first implanted biocompatible polymer matrix is visualized, and a delivery device is directed to the site, and wherein an additional volume of prepolymer solution is delivered incrementally to the site, the prepolymer solution bonding to the periurethral tissue and a previously formed biocompatible polymer mass.

The invention also includes a method for treating GERD in a mammal comprising the steps of delivering a composition comprising a biocompatible prepolymer, a biocompatible solvent, and a contrast agent to the gastroesophageal tissue of the mammal, wherein the prepolymer reacts with all available water at the site of injection and further wherein the delivery results in a polymer matrix of fixed volume formed in situ in the esophageal tissue thereby reducing GERD in the mammal. The method may include the step of delivering the composition into the gastroesophageal tissue by an endoscope.

The invention also includes a method for the delivery of a composition, wherein said composition includes a biocompatible prepolymer, a biocompatible solvent, and a water soluble contrast agent to the gastroesophageal tissue of a mammal, and wherein said tissue already had deposited therein an initial amount of the deposited composition, which method further comprises the steps of visualizing the position of the deposited composition in the esophageal tissue; delivering a prepolymer composition to the esophageal tissue of a mammal containing the deposited composition; reacting the biocompatible polymer with all available water at the delivery site; and delivering additional polymer matrix bonds to the deposited composition incrementally to controllably increase the resistance of the flow of gastric juices from the stomach of the mammal. The method may include the step of: visualizing the deposited composition by selection of one of the processes of the group consisting of direct visualization, feel, fluoroscopy or ultrasound.

The invention also includes a method for further treating GERD in a mammal, comprising the steps of implanting a first biocompatible polymer matrix to a gastroesophageal tissue site of a mammal; implanting a second biocompatible polymer matrix to the site at least 24 hours (one day) after the first implanted biocompatible polymer matrix has been implanted at the site, wherein the implanted biocompatible polymer matrix is visualized; and directing a delivery device to the site, and incrementally delivering an additional volume of prepolymer solution incrementally to the site, the additional volume of prepolymer solution bonding to esophageal tissue and any previously formed biocompatible polymer mass.

DETAILED DESCRIPTION OF THE INVENTION

This invention is directed to methods for augmenting tissue, and specifically for treating urinary incontinence and GERD, which methods comprise delivery of a composition comprising a biocompatible tissue-reactive prepolymer, an inert viscosity lowering medium, and a contrast agent to a tissue site. The tissue-reactive prepolymer types disclosed here differ from inert polymers, in that they bond with tissue to form a bulk inert polymer in situ. The invention further comprises prepolymer preparations, and their use in treating medical conditions.

The term "biocompatible tissue-reactive prepolymer" refers to non-peptidyl prepolymers which, in the amounts employed, are after curing non-toxic, non-migratory, chemically inert, and substantially non-immunogenic when used internally in a mammal; and wherein said prepolymers are substantially insoluble in the internal tissue, for example the periurethral tissue. The bonded biocompatible polymer does not substantially change volume over time and does not migrate to distant organs within the body.

A uniquely flexible, biocompatible, non-biologic tissue bond can be produced by cross-linking hydrated polymer gels to nitrogenous components found in living tissue. The hydrated tissue augmentation is formed by reacting polymeric monomer units with tissue, at least 75% of which are oxyethylene-based dials or polyols with molecular weight exceeding 10,000. The prepolymer is preferably comprised of hydroxyl groups of diols or polyols substantially all capped by polyisocyanate, where non-polymerized polyisocyanate accounts for less than 4% (v/v) of the adhesive tissue augmentation injectable. Amines in the tissue serve to polymerize tissue with the adhesive tissue augmentation injectable. Water mixed with the prepolymer during injection, or acquired at the bond site, generates additional amine through reaction with polyisocyanate and serves to polymerize the bulk of the bond.

The addition of an organic liquid lacking an accessible OH, and preferably one formed in the Krebs cycle, can be used to adjust cure time and prepolymer viscosity. The organic liquid must be completely miscible with the prepolymer, and essentially polar. When the addition liquid is miscible it also becomes trapped permanently within the hydrated polymer matrix formed when injected into tissue. Trapping the addition liquid is essential to preserving hydrated polymer matrix volume. Liquids not occurring naturally within the body may also be used, such as glycerol, but these liquids may not share the same biocompatibility. or may be overly reactive with the prepolymer.

The addition of aqueous solution to the prepolymer just before application represent an embodiment of the present invention, and in the case of aliphatic prepolymer compositions, typically provide long (>10 minutes) pot life, where "pot life" is defined as that period of time just after introduction of the aqueous component to the polyol and just before gelation sufficient to prevent ejection through the treatment needle.

Any of the previously known tissue bulking compositions can be combined with the present invention. Some of these must be added just prior to injection, such as any of several animal components, be they autologous or xenologous. In particular, collagen may be used. All inert additives may be added during device packaging, and form the original ingredients of the composition. For example, teflon particles and fibers, pyrolytic carbon coated beads, silicone beads, etc may be added to the composition. Also, tissue initiators may be added. For example, beta-glucan may be added to promote fibrosis. However, all of the above additions are likely to promote tissue reaction, and therefore must be considered less biocompatible. Also, materials containing groups reactive with isocyanates, such as hydroxyl and amine groups, should not be mixed with the isocyanate-containing prepolymers until just before use.

The diols and polyols used in the tissue bond predominately or exclusively are polyoxyalkylene diols or polyols whose primary building blocks are ethylene oxide monomer units. Preferably, 75% of the units should be ethylene oxide. Other adhesive tissue augmentation injectable systems may contain proportions of propylene oxide or butylene oxide units in the polyols. The use of substantial amounts of butylene oxide subunits is less preferred, and is normally avoided in the present invention.

To obtain desirable tissue augmentation injectable viscosity and bond strength high molecular weight ethylene oxide-based diol and polyols are used to prepare the tissue augmentation injectable. The diol or polyol molecular weight prior to capping with polyisocyanate should be at least 8000 MW, preferably greater than 10,000 MW. Triols (trihydroxy compounds) in the preparation of the polyols are the precursors to preparation of the prepolymer of this invention. There are many suitable triols; examples include, without limitation, triethanolamine, trimethylolpropane, trimethylolethane, and glycerol. Alternatively, tetrols may be used. Triol- or tetrol-based polyols are capped with polyfunctional isocyanate, preferably a diisocyanate.

Alternatively, diols may be used. High molecular weight ethylene oxide-based diols are satisfactory. Diols are to be end capped with diisocyanates in addition with cross-linking compounds. Polyfunctional amines and isocyanates are suitable as cross-linking agents. Mixtures of diols and polyols are also suitable.

The prepolymer of this invention is formed by reacting the hydroxyl groups of the diols or polyols with polyisocyanates. The choice of the polyisocyanate will depend on factors well known in the art, including precursor choice, cure time, and mechanical properties of the tissue bond formed by reacting the prepolymer with tissue.

The choice of precursor is not independent of the choice of polyisocyanate. The choice must afford sufficient cross-linking to the tissue so as not to compete detrimentally with internal cross-linking initiated with the addition of water to the bond. This competition can be favorably biased in favor of the tissue bonding reaction by heating the tissue augmentation injectable, reducing its viscosity by addition of solvents, or adding macroscopic hygroscopic fillers. The choice may also afford rapid bulk polymerization—typically less than 60 seconds. However, in the case of urethral or esophageal bulking a longer pot time is desired, typically about 15-30 minutes. Increase in bulk polymerization time can be accomplished by adding acetone or selecting a less reactive polyisocyante.

Aliphatic or cycloaliphatic polyisocyanates are preferred in the above embodiments because they result in more biocompatible prepolymers and/or longer pot life.

Examples of suitable polyfunctional isocyanates are found in the literature, and include, without limitation, the following polyisocyanates and commonly obtained mixtures of the following (listed alphabetically):

9,10-anthracene diisocyanate; 1,4-anthracene diisocyanate; benzidine diisocyanate; 4,4'-biphenylene diisocyanate; 4-bromo-1,3-phenylene diisocyanate; 4-chloro-1,3-phenylene diisocyanate; cumene-2,4-diisocyanate; Cyclohexylene-1,2-diisocyanate; Cyclohexylene-1,4-diisocyanate; 1,4-cyclohexylene diisocyanate; 1,10-decamethylene diisocyanate; 3,3'dichloro-4,4'-biphenylene diisocyanate; 4,4'diisocyanatodibenzyl; 2,4-diisocyanatostilbene; 2,6-diisocyanatobenzfuran; 2,4-dimethyl1,3-phenylene diisocyanate; 5,6-dimethyl1,3-phenylene diisocyanate; 4,6-dimethyl1,3-phenylene diisocyanate; 3,3'-dimethyl-4,4'diisocyanatodiphenylmethane; 2,6-dimethyl-4,4'-diisocyanatodiphenyl; 3,3'-dimethoxy-4,4'-diisocyanatodiphenyl; 2,4-diisocyantodiphenylether; 4,4'-diisocyantodiphenylether; 3,3'-diphenyl-4,4'-biphenylene diisocyanate; 4,4'-diphenylmethane diisocyanate; 4-ethoxy-1,3-phenylene diisocyanate; Ethylene diisocyanate; Ethylidene diisocyanate; 2,5-fluorenediisocyanate; 1,6-hexamethylene diisocyanate; Isophorone diisocyanate; 4-methoxy-1,3-phenylene diisocyanate; methylene dicyclohexyl diisocyanate; m-phenylene diisocyanate; 1,5-naphthalene diisocyanate; 1,8-naphthalene diisocyanate; polymeric 4,4'-diphenylmethane diisocyanate; p-phenylene diisocyanate; p,p',p''-triphenylmethane triisocyanate; Propylene-1,2-diisocyanate; p-tetramethyl xylene diisocyanate; 1,4-tetramethylene diisocyanate; 2,4,6-toluene triisocyanate; trifunctional trimer (isocyanurate) of isophorone diisocyanate; trifunctional biuret of hexamethylene diisocyanate; and trifunctional trimer (isocyanurate) of hexamethylene diisocyanate.

In terms of commercial availability and regulatory approval, isophorone diisocyanate is preferred for long pot life, and toluene diisocyanate if preferred for quickly reacting diisocyanate.

Bulk curing of the tissue bond of this invention is achieved by using stoichiometric amounts of reactants. The isocyanate-to-hydroxyl molecule ratio should be as low as possible without inhibiting bonding function, typically having values in the range of 1.0 (one polymer hydroxyl group per isocyanate group) up to about 1.1 OH/NCO—i.e., the solution should have all hydroxyls capped and have a small but limited amount of excess isocyanate precursor. Higher ratios achieve adequate bonds but result in excessive amounts of isocyanate monomer in the bond. The time period used to cap the polyol or diol is dependent on the polyisocyanate used. Methods for polyisocyanate capping of polyols are well known.

In forming the tissue augmentation, organic solvents are optionally present during the polymerization with tissue to enable a greater tolerance of excessive isocyanate that may disrupt hydrated polymer formation. Varying the amount of solvent also varies the viscosity of the tissue augmentation injectable. The porosity of the tissue bond can be decreased by reducing the viscosity of the prepolymer, and conversely. Useful solvents are ethanol, acetonitrile, saline and acetone.

A prepolymer may be premixed with aqueous solution in ratios up to about 1:20, more preferably in the range of about 1:1 to 1:10, to initiate polymerization and curing. Alternative, the prepolymer may be delivered to the site and then followed with an injection of difunctional amine to initiate bulk polymerization. Such methods are useful in obtaining near instantaneous tackiness and fixation.

The prepolymer-to-aqueous solution ratio should be in the range of about 3:1 to about 1:20, preferably about 1:5 to about 1:10. The ratio is often chosen such that the in situ cured mass has a modulus that approximates the surrounding tissue modulus. Bulk polymerization time, bond strength and bond porosity each tend to increase when the prepolymer content increases.

The implantability of the cured prepolymer of this invention relates to the bond's ability to present a surface of water to adjacent tissue. When the prepolymers of this invention are used in contact with water-containing tissues, the ethylene oxide segments of the bond attract and complex with water molecules. Consequently, the surface presented to living cells is predominately a layer of water. The protective layer of water renders the underlying synthetic polymeric tissue bond noninteractive with proteins. Consequently, the cured prepolymer does not remove or denature proteins from the environment in which it is implanted.

The prepolymer may also be mixed with a contrast agent or radiopaque material. The contrast agent may become part of the polymer matrix as are the water miscible types, or suspended in the polymer matrix as in the water insoluble type. Water soluble contrast agents include metrizamide, iopamidol, iothalamate sodium, iodomide sodium, and meglumine. Examples of water insoluble contrast agents include tantalum, tantalum oxide, gold, tungsten, platinum, and barium sulfate.

The examples that follow are given for illustrative purposes and are not meant to limit the invention described herein.

EXAMPLE I

Preparation of Tissue Augmentation Injectable A

Pluracol V10™ (BASF, propylene oxide/ethylene oxide) is to be deionized and dried. 2167.3 g deionized Pluracol V10 are to be mixed with 148.5 g isophorone diisocyanate (IPDI) and 0.84 g Santonox® (Monsanto Chemical Co.) and heated at 67 degrees C. under dry nitrogen for 17 days, or until isocyanate concentration reaches 0.4 meq/g. The appearance is clear, with a viscosity of 78,000 cps at 22.degree. C. and 1.1 g/ml at 22.degree. C. and free IPDI of approximately 1.5-3% (wt.). The mixture is decanted and 100 g of meglumine and 100 g of acetone are mixed until in solution. The resulting prepolymer will be radiopaque, low viscosity and form a hydrated matrix trapping acetone when mixed with water or injected into living tissue.

EXAMPLE II

Preparation of Tissue Augmentation Injectable B

Pluracol V10™ (BASF, propylene oxide/ethylene oxide) is to be deionized and dried. 2170 g deionized Pluracol V10 are to be mixed with 82.4 g IPDI, 150 ml butadione. The mixture is to be heated to 67 degrees C. under dry nitrogen until isocyanate concentration reaches 0.2 meq/g.

EXAMPLE III

Preparation of Tissue Augmentation Injectable C

AO-MAL20™ (Shearwater Polymers, Inc., copolymer of M-PEG Allyl Ether and Maleic anhydride) is to be deionized and dried. 900 g deionized TPEG 15000 are to be mixed with 45 g IPDI and 0.6 g Santonox R. To this mixture 500 ml acetonitrile is to be added to obtain a liquid. The mixture is to be heated to 72 degrees C. under dry nitrogen until isocyanate concentration reaches 0.13 meq/g. To this mixture an additional 100 ml of 0.9% saline is added and 50 g barium sulfate.

EXAMPLE IV

Preparation of Tissue Augmentation Injectable D

TPEG1000™ (Union Carbide Corp., polyethylene glycol) is to be deionized and dried. 1475 g deionized TPEG 10000 are to be mixed with 102.3 g IPDI and 0.79 g Santonox R. The reactants are to be dissolved in 87 ml acetonitrile. The mixture is to be heated to 72 degrees C. under dry nitrogen until isocyanate concentration reaches 0.43 meq/g. To this mixture 100 g of dry glycerol are added and mixed.

EXAMPLE V

Preparation of Tissue Augmentation Injectable E

BASF#46889 (polyethylene glycol) is to be deionized and dried. 567 g deionized BASF#46889 are to be mixed with 59 g IPDI and 0.54 g Santonox R. The reactants are to be dissolved in 572 ml acetonitrile. The mixture is to be heated to 67 degrees C. under dry nitrogen until isocyanate concentration reaches 0.46 meq/g.

EXAMPLE VI

Preparation of Tissue Augmentation Injectable F

TPEG 10000™ (Union Carbide Corp., polyethylene glycol) is to be deionized and dried. 475 g deionized TPEG 10000 are to be mixed with 102.3 g IPDI and 0.79 g Santonox R. The mixture is to be heated to 72 degrees C. under dry nitrogen until isocyanate concentration reaches 0.46 meq/g. To this mixture 100 g of acetone are to be added to form a liquid at room temperature.

EXAMPLE VII

Preparation of Tissue Augmentation Injectable G

Polyethylene glycol (PEG) (12000 MW) is to be deionized and dried. 0.03 moles PEG are to be mixed with 0.15 moles trimethylolpropane and heated to 60 degrees C. The heated mixture is to be combined, by stirring for one hour, with 0.11 moles commercial isomer blend of xylene diisocyanate. Stirring is to continue until the isocyanate concentration reaches an asymptote of 0.39 meq/g.

EXAMPLE VIII

Preparation of Tissue Augmentation Injectable H

Polyethylene glycol (PEG) (28000 MW) is to be deionized and dried. 0.04 moles PEG are to be mixed with 0.2 moles trimethylolpropane and heated to 60 degrees C. The heated mixture is to be combined, by stirring for one hour, with 0.1 moles commercial isomer blend of xylene diisocyanate. Stirring is to continue until the isocyanate concentration reaches an asymptote of 0.2 meq/g.

EXAMPLE IX

Preparation of Tissue Augmentation Injectable I

An adhesive tissue augmentation injectable is to be formed by following Example I, substituting an equivalent molar amount of commercial isomer blend of Toluene diisocyanate for the IPDI. The isocyanate content is to reach 0.8 meq/g. The appearance should be a light amber liquid of about 10,000 cps, containing less than 3.5% free TDI.

EXAMPLE X

Preparation of Tissue Augmentation Bond A

Five grams of Adhesive tissue augmentation injectable A are to be mixed with 1 g water for about 1 minute. The pot time of such a tissue augmentation injectable mixture is about 1 hr. The mixture is to be applied to living tissue. The cross-linked structure of tissue and tissue augmentation injectable A are Tissue Bond A.

EXAMPLE XI

Preparation of Tissue Augmentation Bond F

Adhesive tissue augmentation injectable G is to be applied directly to a tissue surface and mixed at the site with liquid present to reach a mixture of 1:5 water-to-tissue augmentation injectable. The cure time is 30-60 seconds. The cross-linked structure of tissue and Adhesive tissue augmentation injectable G are Tissue Bond F.

EXAMPLE XII

Preparation of Tissue Augmentation Bond C

Adhesive tissue augmentation injectable I is to be heated to 65-80 degrees C. and applied directly to a tissue surface. The cure time is 30 seconds. The cross-linked structure of tissue and Adhesive tissue augmentation injectable I are Tissue Bond C.

EXAMPLE XIII

Preparation of Tissue Augmentation Bond D

The tissue surface is to be swabbed with 3% hydrogen peroxide until the surface appears white. The treated surface is to be swabbed dry. Adhesive tissue augmentation injectable I is to be heated to 65-80 degrees C. and applied directly to a tissue surface. Preferably the adhesive layer on the tissue measures less than 1 mm in thickness. A second coat of saturated lysine solution is to be sprayed, but not mixed on the site. Fixing power is achieved immediately. The cross-linked structure of activated tissue, Adhesive tissue augmentation injectable I, and lysine are Tissue Bond D.

EXAMPLE XIV

Preparation of Tissue Augmentation Bond E

Example XIII if followed except Adhesive tissue augmentation injectable I is premixed with equal volumes of acetonitrile and sprayed on the activated site. The cross-linked structure is adhesive immediately, but the acetonitrile is allowed to evaporate to create Tissue Bond E, a thin sealing layer.

Methods Specific to the Treatment of Urinary Incontinence and GERD

The Tissue Augmentation Prepolymers described above can be employed in methods for treating urinary incontinence and GERD in mammals. In the methods for treatment of incontinence the composition is injected into the periurethral tissue via conventional catheter or needle technology using, for example, endoscopic or cystoscopic techniques. The injection can be accomplished with a puncture needle or spinal needle introduced directly or periurethrally with a spinal needle placed percutaneously at the introitus and positioned in the tissue adjacent to the urethra. Alternatively, the periurethral tissue can be exposed surgically and the composition injected directly. Alternatively, the submucosa can be injected using a William's cystoscopic needle. Alternatively, the gastroesophageal junction may be bulked by injection into the esophageal wall via access inside the esophagus.

Injection of the composition into the target tissue causes the composition to gel but not change volume. The formed polymer matrix in the target tissue maintains the tissue in the swelled state, restricts the urethral or esophageal orifice and impedes involuntary flow of urine or gastric juices from the bladder or stomach. The formed injection does not change shape, and is fully elastic. Collagen and particulate injections can change shape, and consequently suffer diminished effectiveness. The particular amount of composition employed is dictated by the level of pre-existing support of the target tissue and not dependent upon the concentration of the prepolymer in the composition or the rate of matrix formation.

The presence of the contrast agent can assist monitoring of the delivery while it takes place by fluoroscopy or ultrasound. Monitoring the delivery of the bulking composition is important to ensure the optimal location in the target tissue is found and an optimal size of polymer matrix is formed.

The components of the injectable composition intended to aid in delivery ideally do not react with the isocyanate component. Similarly, delivery devices should not react with the injectable. Polyethylene syringes and stainless steel hypodermic needles are acceptable in the presence of the composition described herein. Other materials compatible with the compositions described here include polyolefins, fluoropolymers, or silicones.

The methods of this invention are preferably practiced using a kit containing a sealed syringe loaded with a prepolymer composition and a needle of suitable length and gauge. Either the needle produces an opening in the sealed syringe to allow delivery of its contents, or the syringe is sealed with a removable cap, the cap being one with a Luer Lok™ interface with the syringe.

The principles, preferred embodiments and modes of operation of the present invention have been described in the foregoing specification. The invention that is intended to be protected herein, however, is not to be construed as limited to the particular forms disclosed, since these are to be regarded as illustrative rather than restrictive. Variations and changes may be made by those skilled in the art without departing from the spirit of the invention.

The invention claimed is:

1. A hydrated, biocompatible tissue-reactive composition comprising:
    at least one NCO-terminated hydrophilic urethane prepolymer derived from reaction of an organic polyisocyanate with oxyethylene-based diols or polyols in an isocyanate-to-hydroxyl ratio ranging from about 2.0 to about 2.5;
    wherein essentially all hydroxyl groups are capped with polyisocyanate, in which the average molecular weight of said polyisocyanate capped prepolymer is at least 3,000,
    wherein the oxyethylene-based diols or polyols have an average molecular weight ranging from about 3,000 to about 30,000, and
    wherein an isocyanate concentration in the prepolymer is between 0.05 and 0.8 milliequivalents per gram, and
    an aqueous solution in a prepolymer-to-aqueous solution ratio of about 1:10 to about 1:20.

2. The hydrated, biocompatible tissue-reactive composition of claim 1 in which the diols or polyols are capped with polyisocyanate so that isocyanate groups are in excess by no more than about 10% compared to the number of hydroxyl groups on the polyols.

3. The hydrated, biocompatible tissue-reactive composition of claim 1 that further comprises an aqueous solution mixed with the prepolymer just before administration.

4. The hydrated, biocompatible tissue-reactive composition of claim 3 that contains 10% to 95% by weight of an isotonic saline solution.

5. The hydrated, biocompatible tissue-reactive composition of claim 1 that includes an injectable material selected from the group comprised of collagen, silicone, Teflon, and pyrolytic carbon coated beads.

6. The hydrated, biocompatible tissue-reactive composition of claim 1, wherein the oxyethylene-based diols or polyols are selected from oxyethylene-based triols.

7. A hydrated, biocompatible tissue-reactive composition comprising:
    at least one NCO-terminated hydrophilic urethane prepolymer derived from reaction of an organic polyisocyanate with oxyethylene-based diols or polyols in an isocyanate-to-hydroxyl ratio ranging from about 2.0 to about 2.5;
    wherein essentially all hydroxyl groups are capped with polyisocyanate, in which the average molecular weight of said polyisocyanate capped prepolymer is at least 3,000;
    wherein the oxyethylene-based diols or polyols have an average molecular weight ranging from about 3,000 to about 30,000; and
    an aqueous solution in a prepolymer-to-aqueous solution ratio of about 1:10 to about 1:20, wherein the aqueous solution is mixed with the prepolymer just before administration; and
    about 10% to about 95% by weight of an isotonic saline solution.

8. The hydrated, biocompatible tissue-reactive composition of claim 7 in which the diols or polyols are capped with polyisocyanate so that isocyanate groups are in excess by no more than about 10% compared to the number of hydroxyl groups on the polyols.

9. The hydrated, biocompatible tissue-reactive composition of claim 7 in which the isocyanate concentration in the prepolymer units is between 0.05 and 0.8 milliequivalents per gram.

10. The hydrated, biocompatible tissue-reactive composition of claim 7 that includes an injectable material selected from the group comprised of collagen, silicone, Teflon, and pyrolytic carbon coated beads.

11. The hydrated, biocompatible tissue-reactive composition of claim 1, wherein the oxyethylene-based diols or polyols is selected from oxyethylene-based triols.

* * * * *